United States Patent [19]

Steuernagel et al.

[11] 4,334,076

[45] Jun. 8, 1982

[54] PROCESS FOR THE PREPARATION OF SULFURIC ACID SEMIESTER ETHYLSULFONYL COMPOUNDS OF AMINOPHENOLS, AMINOBENZANILIDES OR PHENYLPYRAZOLONES BY ESTERIFICATION WITH SULFURIC ACID AND/OR SULFUR TRIOXIDE IN A KNEADER

[75] Inventors: Hans H. Steuernagel, Kelkheim; Ernst Hoyer; Fritz Meininger, both of Frankfurt am Main, all of Fed. Rep. of Germany

[73] Assignee: Hoechst Aktiengesellschaft, Frankfurt am Main, Fed. Rep. of Germany

[21] Appl. No.: 820,884

[22] Filed: Aug. 1, 1977

[30] Foreign Application Priority Data

Aug. 3, 1976 [DE] Fed. Rep. of Germany ....... 2634783
Aug. 3, 1976 [DE] Fed. Rep. of Germany ....... 2634856
Aug. 3, 1976 [DE] Fed. Rep. of Germany ....... 2634857

[51] Int. Cl.$^3$ ................. C07C 139/00; C07C 139/10; C07D 231/02; C07D 231/34
[52] U.S. Cl. ..................................... 548/375; 260/147; 260/148; 260/150; 260/162; 260/163; 260/194; 260/195; 260/197; 260/198; 260/199; 260/200; 260/201; 260/202; 260/203; 260/204; 260/208; 260/458 C
[58] Field of Search .................. 260/458 C, 208, 162, 260/163; 548/375

[56] References Cited

U.S. PATENT DOCUMENTS 2,666,788  1/1954  Ebel ..................................... 260/556
2,912,428  11/1959  Gaertner et al. ..................... 260/152
3,193,546  7/1965  Freyermuth et al. ................ 260/200
3,483,182  12/1969  Sugiyama et al. ................... 260/163
3,859,271  1/1975  Sugiyama et al. ................... 260/163
3,859,324  1/1975  Bloch .................................. 260/457
3,956,267  5/1976  Sommer et al. ...................... 260/165

Primary Examiner—Floyd D. Higel
Attorney, Agent, or Firm—Curtis, Morris & Safford

[57] ABSTRACT

An improved and novel process had been found for the esterification of aminophenol, amino-benzanilide and pyrazolone compounds containing a β-hydroxyethylsulfonyl group, by means of sulfuric acid or sulfur trioxide which improvement is characterized by that the esterification is performed in a machine which is operating with a kneading action and effect, using per mol β-hydroxyethylsulfonyl compound 1 to 2.5 times the equivalent molar amount of concentrated sulfuric acid, oleum or sulfur trioxide. This novel process has the great advantage that great amounts of sulfuric acid are saved which could charge the waste water, also in form of sodium sulfate formed after the required neutralization. Furthermore, the β-sulfatoethylsulfonyl compounds formed as end-products in the esterification process are prepared by this novel process in higher yields, in a higher degree of esterification rate and in a higher purity. They are obtained in form of a powder or plastic mass from the kneading machine, which is well transportable and storable, and can advantageously used in the form of this consistency, without intermediate isolation of the pure β-sulfato compound itself, directly for the preparation of azo dyestuffs which are poor of inert salts, possess a high tinctorial strength and purity.

13 Claims, No Drawings

PROCESS FOR THE PREPARATION OF SULFURIC ACID SEMIESTER ETHYLSULFONYL COMPOUNDS OF AMINOPHENOLS, AMINOBENZANILIDES OR PHENYLPYRAZOLONES BY ESTERIFICATION WITH SULFURIC ACID AND/OR SULFUR TRIOXIDE IN A KNEADER

The present invention relates to an improved process for the preparation of a sulfuric acid semi-ester compound of the following formula (II) by esterification of a compound of the following formula (I)

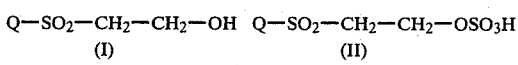

or a salt thereof.
wherein the reaction is carried out with 1 to 2.5 times the equimolar amount, calculated on one mol of $SO_3$, of 92 to 100% strength sulfuric acid or of sulfur trioxide or of sulfuric acid containing sulfur trioxide, in a machine operating with a kneading action and effect.

In these formulae (I) and (II), the radicals Q- represent a radical of the formula (A), (B) or (C)

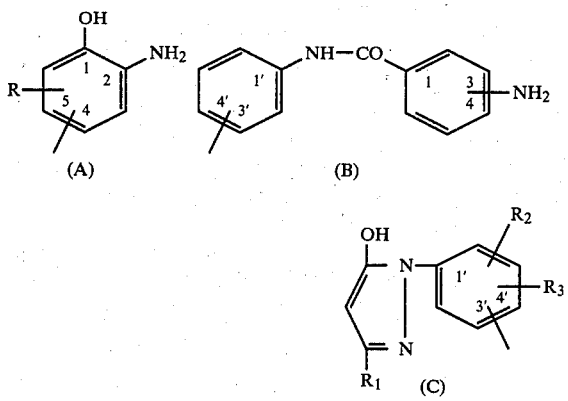

in which
R represents a hydrogen atom, a lower alkoxy group, such as a methoxy or ethoxy group, especially the methoxy group, a lower alkyl group, such as a methyl or ethyl group, especially the methyl group, the nitro group or a chlorine or bromine atom, especially a bromine atom; the β-hydroxy or β-sulfatoethylsulfonyl group in the radical of formula (A) is in the 4- or 5-position of the benzene nucleus; in formula (B), the β-hydroxy- or β-sulfatoethylsulfonyl group stands in the 3'- or 4'- position of the anilide radical and the amino group stands in the 3- or 4-position of the benzoyl radical;
$R_1$ represents a methyl, carboxyl or phenyl group, $R_2$ represents a hydrogen atom, a methyl, ethyl, methoxy or ethoxy group or a chlorine atom, $R_3$ represents a hydrogen atom, a methyl, ethyl, methoxy or ethoxy group;
the β-hydroxy- or β-sulfatoethylsulfonyl group in formula (C) stands in the 3'- or 4'-position of the benzene nucleus.
The preparation of the compounds:
2-aminophenol-4-β-sulfatoethylsulfone,
2-aminophenol-5-β-sulfatoethylsulfone,
2-amino-4-methyl-5-β-sulfatoethylsulfonylphenol,
2-amino-4-methoxy-5-β-sulfatoethylsulfonylphenol,
4-amino-3'-(β-sulfatoethylsulfonyl)-benzanilide,
1-[4'-(β-sulfatoethylsulfonyl)-phenyl]-3-methyl-pyrazol-5-one
according to the process of the invention is particularly preferred.

The compounds of the formula (II) are suitable as preproducts (diazo components or coupling components) for the preparation of azo dyestuffs, as known in the art.

The conversion of compounds of the formula (I) into compounds of the formula (II) is known per se. However, the hitherto described methods require large excesses of sulfuric acid which have to be diluted with water and/or neutralized either during work up of the esterification product of the formula (II) and its isolation, or during further processing of this product to form dyestuffs, and removed from this starting material or from the dyestuff. Recovery of the sulfuric acid is thus partically impossible. In addition, the acids as such, or in neutralized form as soluble sulfates, contaminate the sewage.

Furthermore, the known esterification processes have the disadvantage that the compounds of the formula (II) are produced as solutions in sulfuric acid; these solutions are, however, not very well suited to storing, for example, for later processing, and must if necessary be further processed immediately to form the corresponding dyestuffs.

Thus, for example, the esterification of a compound of the formula (IA), for example according to German Pat. No. 953 103, Example 5, is effected with 6 times the molar amount of concentrated sulfuric acid.

After diluting the sulfuric acid solution with a large amount of ice and water, the amino group is diazotized and the diazonium compound, after neutralization of the large excess of sulfuric acid to neutral sodium sulfate, is coupled with a coupling component to form an azo dyestuff which is subsequently converted into its chromium complex compound. The resulting chromium complex dyestuff is separated by the addition of sodium chloride, freed whereby the dyestuff solution is freed of the high sulfate content, and filtered.

The procedure in German Pat. No. 1 012 010, Examples 1 to 4, and in German Pat. No. 1 126 542, Examples 1 to 4 and 6, are similar.

Likewise, esterification of a compound of the formula (IB), for example, according to German Pat. No. 1 126 547, Examples 1 and 2, is carried out with 15 times the molar amount of concentrated sulfuric acid. The procedure in German Auslegeschrift No. 1 206 107, Examples 1 and 2, and in German Auslegeschrift No. 1 206 108, Examples 1 and 2, is similar.

Likewise, esterification of a compound of the formula (IC) for example according to German Offenlegungsschrift No. 1 804 524, Example 2 or 5, is carried out with 7 times the molar amount of concentrated sulfuric acid.

After diluting the sulfuric acid solution with a large amount of ice and water and after neutralization of the large excess of acid, the ester compound obtained is coupled with a diazonium compound to form an azo dyestuff, which is then separated by the addition of sodium chloride or potassium chloride, thus been freed of the high sulfate content, and filtered.

The sodium sulfate remaining in the mother liquor and the sodium or potassium chloride introduced in addition in order to salt out the dyestuff, results, however, in charging the sewage from the processes mentioned with a considerable amount of salt.

The procedure in German Auslegeschrift No. 1 215 282, Examples 1 and 2, and in German Offenlegungsschrift No. 2 009 421, Example 11, are similar but the amounts of sulfuric acid used are larger. In Example 1 of the German Offenlegungsschrift No. 2 009 421, the isolation of the dyestuff produced from the esterified coupling component is effected by subjecting the dyestuff solution together with the sodium sulfate derived from 13 times the molar excess of sulfur, to spray-drying. The dyestuff powder obtained in this manner is, however, very weak in color and has a high percentage content of neutral salts (electrolytes), and in this form would scarcely be of interest for commercial use.

Although neutralization of the excess sulfuric acid with calcium carbonate and filtering off the difficulty soluble calcium sulfate, as described, for example, in Example 3 of German Pat. No. 953 103 reduces the load in the sewage, additional expenditure on labour and material are necessary for this purpose; furthermore, this method has the disadvantage that the gypsum thus produced must be dumped as useless industrial refuse.

Furthermore, it is known from German Offenlegungsschrift No. 1 443 877, Example 3, that compounds of the formula IB can be converted, with 3 times the equimolar amount of amidosulfonic acid in pyridine, into their sulfuric acid semi-esters of the formula (IIB). Although this means there is a clear reduction of the excess of esterification agent, the pyridine used must subsequently be substantially distilled off under reduced pressure. Nevertheless approximately a quarter of the pyridine introduced still passes, during further processing of the sulfuric acid semiester to form the dyestuff preparation, into the mother liquor from which it must be removed in some manner before this waste water can be allowed to pass into the sewage system.

There was therefore an urgent need for an esterification process which avoids these disadvantages and results in practically no, or substantially reduced pollution of the environment.

An improved process for the esterification of the above-mentioned aromatic amines and pyrazolones of the formulae (IA), (IB) and (IC) into their sulfuric acid semi-esters of the formulae (IIA), (IIB) and (IIC) has now been found wherein the esterification of a compound of the formula (I) is carried out in a machine operating with a kneading action and effect and with the action of 1 to 2.5 times the equimolar amount, calculated on one mol of $SO_3$, of 92–100% strength sulfuric acid or sulfur trioxide or sulfuric acid containing sulfur trioxide, preferably with a content of up to approximately 70, especially 15–65% by weight of sulfur trioxide.

There are to be understood hereinafter by machines having a kneading action and effect (called kneaders hereinafter), machines which are suitable for mixing, dispersing or homogenising, and which can process together liquid and solid components under high forces. The processing (kneading) is usually carried out under high pressure with the moving parts of the machine, such as rolls, discs, rollers, tightly engaging gears and worms, running in the same or opposite directions, preferably at different speeds, which mix the components together under high pressure, optionally with the application of shearing forces. Examples of such kneaders are, apart from actual kneaders and extruders, saw tooth agitators (dissolvers), rotor-stator mills, dispersing machines (dispergators) and rollers mills. These machines may operate continuously or discontinuously; a large number of them in commercial form are known. Discontinuously operating kneaders are, for example, double-troughed kneaders, such as sigma paddle kneaders, dispersion kneaders, Banbury dispersion mixers, continuously operating kneaders, for example, kneading extruders, and continuous single shaft and multi-shaft kneaders (see in this connection also Ullmanns Encyclopädie der Technischen Chemie, Vol. 1 (1951), pages 725–727; Ullmanns Encyclopädie der Technischen Chemie, 4th Edition, Vol. 2 (1972), pages 23 and 292–299).

The process is carried out in a simple manner either by placing one of the reactants in the kneader and gradually adding the second component or by adding the components to the kneader simultaneously or in the form of a mixture.

The sulfuric acid used in the reaction is preferably in the form of concentrated sulfuric acid (96% strength), in the form of so-called monohydrate (100% strength sulfuric acid) or in the form of oleum. Preferably 1 to 2.2 times, especially 1.0–1.5 times, and more particularly 1.1–1.5 times the equimolar amount, calculated on the mole of $SO_3$, of esterification agent is used to esterify compounds of the formula (I).

To esterify the aminophenol compounds of the formula (IA), the reaction temperature may be between +10° C. and 160° C.; preferably the reaction with sulfuric acid or oleum or sulfur trioxide is carried out in the kneaders at a temperature of 100°–140° C. To esterify the aminobenzanilide compounds of the formula (IB) the reaction temperature may be between +10° C. and 130° C.; preferably the reaction with sulfuric acid or oleum or sulfur trioxide is carried out in kneaders at a temperature of 70°–100° C. Similarly, to esterify the 1-phenylpyrazolone compounds of the formula (IC), the reaction temperature may be between +10° C. and 150° C.; preferably the reaction is carried out at a temperature of 80°–130° C. Generally, the esterification of a compound of the formula (I) to form the compound of the formula (II) is advantageously carried out at a temperature of between 80° and 120° C. The regulation of the temperature is usually effected by means of the cooling and heating jacket of the kneader. The treatment time for the reaction mixture in the kneader can be from a few minutes to several hours, depending on the temperature and kneading intensity as well as on the esterification agent used. Advantageously, for the esterification of the aminophenol compounds of the formula (IA) the temperature is between 110° and 140° C., for the esterification of the aminobenzanilide compounds of the formula (IB), between 70° and 100° C. and for the esterification of the pyrazolone compounds of the formula (IC) between 110° and 130° C., in each case within a reaction and kneading time of 5 minutes to 6 hours, which in these conditions depends in particular on the kneading intensity applied, which in turn depends on the type of machine used.

To improve the kneading action and effect or the heat transfer in the kneading mixture during the kneading operation, it is also possible to incorporate an inert addition agent, such as kieselguhr, talcum or a metal powder, which can be removed again by simple filtration from aqueous solution from the sulfuric acid semi-ester of the formula (II) or from a dyestuff produced therefrom, when working up or further processing of the kneaded material.

The work up of the reaction product after esterification in the kneader is carried out in a manner that is current and customary to a person skilled in the art. Advantageously it is effected by dissolving the reaction product in water with simultaneous neutralization of the solution. The neutralization is preferably carried out with sodium bicarbonate or sodium carbonate. The neutral or very weakly acidic solution is then, optionally after separating off the above-mentioned inert addition substances, for example by filtering or centrifuging, evaporated to dryness or spray-dried. In this manner, for example with neutralization with the abovementioned sodium salts, the compound of the formula (II) is obtained in the form of its sodium salt. Correspondingly it is possible to use potassium bicarbonate or potassium carbonate for neutralization. Another possibility of working up the kneaded material is to neutralize it with calcium carbonate after dissolving in water, filter off with suction the precipitated calcium sulfate and add sodium oxalate or oxalic acid and sodium carbonate or bicarbonate to the filtrate, separate the solution in the usual manner, from the precipitate formed, for example by filtering or centrifuging, and then spray-dry it. With this new esterification process, substantially smaller amounts of gypsum are produced than in hitherto known processes.

An excellent and important advantage of the esterification process of the invention is that it is not necessary to work up the end product. The reaction products leave the kneaders in the form of powders or as small or crumb-like pieces, or in the form of plastic compositions; they may easily be stored and transported in this form. It is possible to process these products by a simple, sewage-free method harmless to the environment, into fiber-reactive azo dyestuffs of the formulae (III) and (IV).

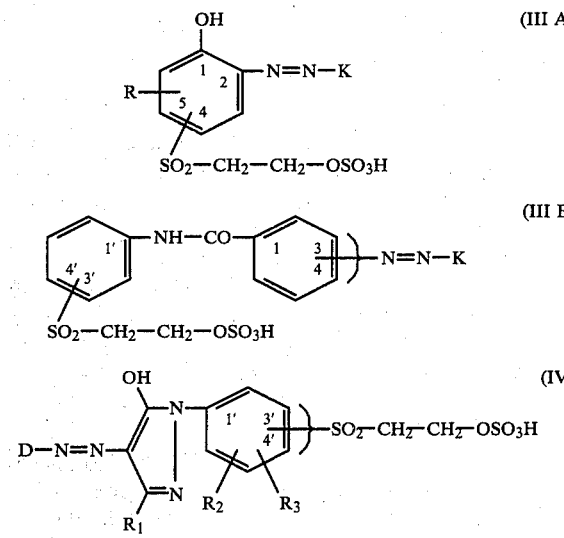

In these formulae
K represents the radical of a coupling component, which may also contain an azo grouping,
D represents the radical of a diazo component
$R$, $R_1$, $R_2$ and $R_3$ have the above-mentioned meaning,
the β-sulfatoethylsulfonyl group in formula (IIIA) stands in the 4- or 5-position of the benzene nucleus,
the azo group in formula (IIIB) stands in the 3- or 4-position of the benzoyl radical,
the β-sulfatoethylsulfonyl group in formula (IIIB) stands in the 3'- or 4'-position of the anilide radical, and
the β-sulfatoethylsulfonyl group in formula (IV) stands in the 3'- or 4'-position of the benzene nucleus.

In the same manner it is possible to process further the reaction products emerging from the kneaders, in a simple, sewage-free manner harmless to the environment, into metal complex compounds of the dyestuffs of the formulae (IIIA) and (IV).

This advantage is as a result of the fact that the process products of the formula (II) obtained according to the esterification process of the invention have a degree of esterification of 95–100% and are obtained in a high yield, yet surprisingly are of even higher quality than those produced according to the known processes. Accordingly, the dyestuffs of the formula (III) and (IV) obtainable from the process products of the esterification process according to the invention are of excellent quality and a high purity of shade when used for dyeing and printing cellulose fiber materials; the dyestuffs are in addition obtained in a high yield calculated on the starting compounds of the above formula (I).

If 1 to approximately 1.5 mole of esterification agent is used per mole of the compound of formula (I), the kneaded material is usually yielded in the form of a powder, and if 1.5 to 2.5 mole of esterification agent is used per mole of the compound of formula (I), it is yielded in powder or in plastic form. The kneaded material obtained in accordance with the invention can be stored and transported without problem, preferably in the form of a powder, in barrels, so that further processing, for example, to form dyestuffs, can be carried out at a time and place independent of the esterification.

For further processing to form azo dyestuffs of the formula (III), the kneaded material is diazotized in an aqueous Congo-acidic solution, wherein one may dispense completely or partially with a further addition of acid, depending on the quantity of esterification agent used in the esterification process. The diazotization is carried out in a known and customary manner, as is also the subsequent coupling with the coupling component of the formula H—K, in which K has the above-mentioned meaning, after establishing an appropriate pH value, to form a dyestuff of the above formula (III). Advantageously the diazotization, especially the diazotization of the amine of the formula (IIB) contained in the kneaded material, is carried out by first dissolving the kneaded material in water until neutral with the addition of an acid-binding agent, such as sodium carbonate or bicarbonate, then adding a very small excess of sodium nitrite with the addition of ice, and adjusting this solution so that it shows a Congo acidic pH-value, by means of an acid such as hydrochloric acid. The diazonium salt thus formed can be coupled without isolation, that is directly in suspension or solution, with the coupling component in the manner mentioned above.

For further processing to form azo dyestuffs of the formula (IV), the kneaded material containing the compound of the formula (IIC), in the form produced or after dissolution in water until neutral with the addition of an acid-binding agent, such as sodium carbonate or bicarbonate, is coupled in a known and customary manner with a diazonium compound of an amino compound of the formula D—NH$_2$, in which D has the above-mentioned meaning, at an appropriate pH-value to form a dyestuff of the formula (IV).

The dyestuff thus obtained of the formula (IIIA) or the dyestuff of the formula (IV) thus produced as far as it contains in the ortho-position of the radical D a substituent capable of metal complex formation, can again be converted in an advantageous manner in the same reaction medium (coupling medium) into its metal complex compound, especially into a copper, cobalt or chromium complex dyestuff by a corresponding metal-donating agent, here, the direct metallization of the dyestuff (in formula (IV) D contains a hydroxy or carboxy group in ortho-position to the azo group) is particularly advantageous on account of the subsequent method of isolation of the dyestuff.

As a result of the relatively low content of sulfate, formed in the esterification reaction, of the dyestuff solution thus produced, it is not necessary to separate the dyestuff by salting out with sodium chloride or potassium chloride and then to filter it, advantageously the weakly acidic to neutral dyestuff solutions, and also the solutions of metal complex dyestuffs obtained by direct metallisation, are directly evaporated to dryness or subjected to spray-drying.

By this method, dyestuff powders are obtained in high yield which possess a high tinctorial strength and an excellent quality and purity, which correspond in their properties to the dyestuff products produced in known manner, but are, in fact generally superior to the latter regarding the degree of esterification of the β-hydroxyethylsulfonyl group, their content of dyestuff, the tinctorial strength, solubility in water and dyestuff yield.

As a result of the good solubility of the dyestuff, the dyestuff solutions produced as described above, can also be used directly for dyeing purposes, if necessary after additionally concentrating to a smaller volume.

The present invention thus also relates to the simplified, advantageously sewage-free preparation of fiber-reactive azo dyestuffs using the products of the formula (II) obtained in the esterification process according to the invention, wherein kneaded material is directly used without isolation of the compound of formula (II), optionally dissolved in water, as diazo component (relating to formula (IIA) and (IIB)) or as coupling component (relating to formula (IIC)), and the diazo component of the formula (IIA) or (IIB) is diazotized according to customary processes and, after establishing a pH value appropriate for an azo coupling, is coupled according to customary processes with a coupling component of the formula H-K, or the compound of the formula (IIC) is coupled with a diazotized amine, the amine having the formula D—NH$_2$, and the azo dyestuff thus obtained is optionally metallized without previous isolation, and subsequently isolated, advantageously by spray-drying or evaporating.

The following Examples serve to illustrate the subject of the invention. The parts by weight referred to therein are to the parts by volume as kilogram to liter. The percentages are percentages by weight where they are not related to the theoretical yield statement.

EXAMPLES GROUP A

Example 1

(a) 2657 parts by weight of 98% (which means a product containing 98% of said benzene compound, the residual 2% being electrolytes, such as sodium chloride), 2-amino-1-hydroxy-4-(β-hydroxyethyl-sulfonyl)-benzene were placed in the form of a dry powder placed in a customary commercial dispersion kneader (for example of the firm Werner and Pfleiderer, Stuttgart-Feuerbach), of which one kneading arm operated at a speed of 29 revs/min and the other at a speed of 21 revs/min. Then, while the machine was running, 1285 parts by weight of 65% strength oleum (that is 65 parts by weight SO$_3$ and 35 parts by weight of H$_2$SO$_4$ per 100 parts by weight of oleum) were introduced over the course of 15 minutes. Subsequently the reaction mixture was processed for a further hour at 120° to 140° C. in the kneader. The kneader was then emptied. 3743 parts by weight of 2-amino-1-hydroxy-4-(β-sulfatoethylsulfonyl)-benzene (93% strength), corresponding to a theoretical yield of 98%, were obtained in the form of a light-grey powder.

(b) 2.0 parts by weight of the kneaded material were stirred, with simultaneous portionwise addition of approximately 0.75 parts by weight of sodium bicarbonate, into a mixture of 8 parts by volume of water and 2 parts by weight of ice at 0° to 5° C. The pH value of the aqueous solution thus obtained was 5.0 to 5.4; the solution was clarified by filtration and evaporated to dryness in vacuo at 40°–50° C. It was ground, and 2.1 parts by weight of a powder were obtained, which contained the pure compound of the formula

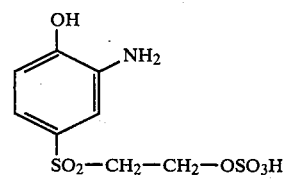

in the form of its sodium salt, together with 9% of sodium sulfate.

Example 2

63.7 parts by weight of the kneaded material produced in Example 1a were dissolved in a mixture of 300 parts by volume of water and 100 parts by weight of ice, and diazotized with 40.1 parts by volume of an aqueous 5 N sodium nitrite solution. A small excess of nitrite still present after the diazotization reaction was destroyed with a little amido-sulfonic acid. Then, 51.8 parts by weight of a 98% 1-(4'-sulfophenyl)-3-methylpyrazol-5-one in the form of a powder were added. A pH of 6 to 6.5 was established and maintained with approximately 17 parts by weight of anhydrous sodium carbonate until the coupling was complete (test on diazonium salt negative). Then, 50 parts by weight of crystalline copper sulfate were added and the pH value was adjusted to 4.5 to 5.0 with 50 parts by weight of crystalline sodium acetate and approximately 14 parts by weight of anhydrous sodium carbonate. The reaction solution was stirred at room temperature for 3 hours, then clarified and evaporated at 50° to 60° C.

The residue was ground; 202 parts by weight of a yellow-brown dyestuff powder were obtained, which powder was 66% by weight of the dyestuff of the formula

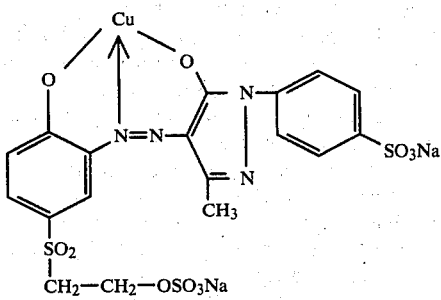

In the presence of an agent having an alkaline action and using dyeing and printing methods known and customary for reactive dyestuffs, this dyestuff dyed cotton and other cellulose fiber materials clear yellow strong shades of very good fastnesses to light and to wetting.

A dyestuff powder of the same dyestuff content and the same good quality is obtained if the clarified dyestuff solution obtained in the preparation is spray-dried instead of evaporated.

Example 3

63.7 parts by weight of the kneaded material produced according to Example 1a were dissolved and diazotized as described in Example 2. The solution of the diazonium salt was coupled with 136.5 parts by weight of 1-acetylamino-8-hydroxynaphthalene-3,6-disulfonic acid (53% strength) at a pH value of 6 to 7. To the resulting solution of the azo dyestuff, having in the form of the free acid the formula

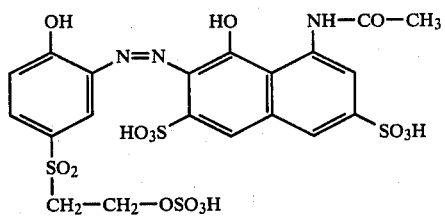

50 parts by weight of chrome alum were added without intermediate isolation of the dyestuff from the solution and the pH value was adjusted to 5.3 to 5.7 with crystalline sodium acetate. Subsequently the reaction mixture was boiled under reflux for approximately 10 hours until there was no more metal-free dyestuff detectable in a chromatogram. The solution of the resulting 1:2 chromium complex dyestuff was clarified by the addition of 10 parts by weight of kieselguhr and then spray-dried. A blue-black dyestuff powder was obtained which yielded on cellulose fiber materials strong marine-blue prints and dyeings of very good-fastness to wetting and to light when applied by dyeing and printing processes, customary and known for reactive dyestuffs, in the presence of an agant having an alkaline action.

Example 4

63.7 parts by weight of the kneaded material produced according to Example 1a were diazotized as described in Example 2. The solution of the diazonium salt was coupled with 45.3 parts by weight of 2-aminonaphthalene-5-sulfonic acid (98.4% strength) at a pH value of 5 to 6. 28.1 parts by weight of crystalline cobalt sulfate were added to this solution of the prepared dyestuff which in the form of the free acid has the formula

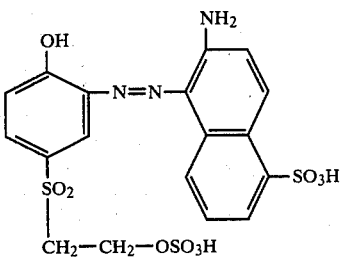

The pH value was adjusted to 5.0 to 5.5 with 40 parts by weight of crystalline sodium acetate and with anhydrous sodium carbonate. The reaction solution was stirred for 1 hour at room temperature until no further metal-free dyestuff could be determined in a chromatogram. The solution of the resulting 1:2 cobalt complex dyestuff was clarified by the addition of 10 parts by weight of kieselguhr and then spray-dried. A black dyestuff powder was obtained which, using the printing and dyeing processes known and customary for reactive dyestuffs, produced deep black prints and dyeings of very good fastness to wetting and to light, on cellulose fiber materials.

Example 5

If the 2657 parts by weight of 2-amino-1-hydroxy-4-($\beta$-hydroxyethylsulfonyl)-benzene in Example 1a are replaced by the equimolar amount of 2-amino-1-hydroxy-5-($\beta$-hydroxyethylsulfonyl)-benzene and the procedure is otherwise the same as in Example 1a, 2-amino-1-hydroxy-5-($\beta$-sulfatoethylsulfonyl)-benzene is obtained in a good yield, likewise in the form of a powder, and has a degree of esterification of 98–99%. It is also possible to isolate 2-amino-1-hydroxy-5-($\beta$-sulfatoethylsulfonyl)-benzene in the form of an alkali metal salt from the kneaded material in a manner analogous to that in Example 1b.

Example 6

2216 parts by weight of 2-amino-1-hydroxy-4-($\beta$-hydroxyethylsulfonyl)-benzene (98% strength) in the form of a dry powder were placed in a customary commercial dispersion kneader (for example of the firm Werner and Pfleiderer, Stuttgart-Feuerbach). With the machine running, 2156 parts by weight of 100% strength sulfuric acid ("monohydrate") were introduced over a period of 20 minutes. The reaction temperature was increased to 130° C. by means of jacket heating and the mixture was left in the running kneader for a further 6 hours at 130° to 140° C. The kneader was then emptied; 4166 parts by weight of 69.6% strength 2-amino-1-hydroxy-4-($\beta$-sulfatoethylsulfonyl)-benzene were obtained. The degree of esterification was 97%.

The product thus obtained can be used for the preparation of reactive dyestuffs in a manner analogous to that described in Examples 2 to 4.

Example 7

16.0 g/min of 2-amino-1-hydroxy-4-($\beta$-hydroxyethylsulfonyl)-benzene (98% strength) in the form of a dry powder were introduced by way of a metering worm, and simultaneously 6.2 ml/min of 65% strength oleum were introduced by means of a metering pump into a customary commercial, continuously operating kneader (for example, the BUSS-Ko kneader, type PR 46 of BUSS AG., Basle, Switzerland) operating at 27 revs/min. The temperature of the kneader was maintained at 130° to 140° C. by means of steam heating the jacket. The kneaded material emerging had a content of 77.6% by weight of 2-amino-1-hydroxy-4-(β-sulfatoethylsulfonyl)-benzene of a molecular weight of 297. The degree of esterification was 97–98%.

The kneaded material obtained can be processed to form reactive dyestuffs in a manner similar to that described in Examples 2 to 4.

Examples 8 to 12

By proceeding in a manner analogous to that described in Examples 1, 6 or 7, using the starting compounds given in the following Table-Examples 8 to 12, the corresponding sulfuric acid semi-esters of the formula given hereinafter (end products) are obtained in a high yield, of high purity and having a high degree of esterification. These sulfuric acid semi-ester compounds are excellently suitable in a known manner, for example, as described in Examples 2 to 4, to form fiber-reactive azo dyestuffs and the metal complex thereof.

compounds of the formula (II) obtained according to the process of the invention without any intermediate isolation. By applying accordingly the methods described in Examples 2 to 4 in that the sulfato compounds are first diazotized, then coupled in the usual manner with the corresponding coupling component given in the Example, then converted by treating with an appropriate metal-donating agent into the corresponding compound of the metal given in the Example and the dyestuff thus obtained isolated by evaporating or spray drying, dyestuff powders are obtained which, when used in printing and dyeing processes known and customary for reactive dyestuffs, yield on cotton dyeings and prints the indicated color shades of which are fast to light and to wetting and of strong color depth.

The compounds (A) and (B) in the Table have the following formulae

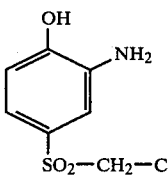

(A)

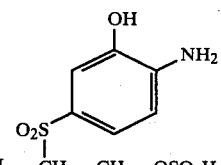

(B)

| Ex | Starting compound | End product |
|---|---|---|
| 8 | OH, NH₂, CH₂—O₂S, CH₃, CH₂, OH | OH, NH₂, CH₂—O₂S, CH₃, CH₂, OSO₃H |
| 9 | OH, NH₂, CH₂—O₂S, OCH₃, CH₂, OH | OH, NH₂, CH₂—O₂S, OCH₃, CH₂, OSO₃H |
| 10 | OH, Br, NH₂, SO₂—CH₂—CH₂—OH | OH, Br, NH₂, SO₂—CH₂—CH₂—OSO₃H |
| 11 | OH, CH₃O, NH₂, SO₂—CH₂—CH₂—OH | OH, CH₃O, NH₂, SO₂—CH₂—CH₂—OSO₃H |
| 12 | OH, O₂N, NH₂, SO₂—CH₂—CH₂—OH | OH, O₂N, NH₂, SO₂—CH₂—CH₂—OSO₃H |

In Examples 8–12 the degree of esterification was in each case 97–99%.

Examples 13 to 29

Furthermore, the metal complex dyestuffs shown in the following Table Examples, were prepared from the

| Ex. | Compound of the Formula II | Coupling component | Metal | Color shade on cotton |
|---|---|---|---|---|
| 13 | (A) | 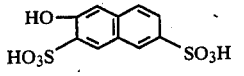 | copper | bluish-red |
| 14 | (A) | 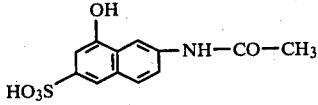 | copper | bluish-red |
| 15 | (A) | 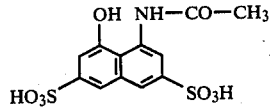 | copper | red-violet |
| 16 | (A) | 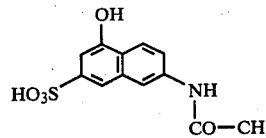 | copper | bluish-red |
| 17 | (A) | 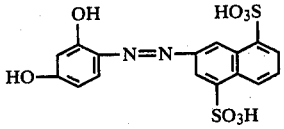 | copper | brown |
| 18 | (B) | " | copper | brown |
| 19 | (B) | 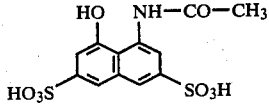 | copper | violet |
| 20 | (B) | 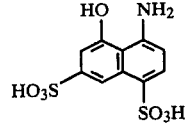 | copper | marine blue |
| 21 | (B) | 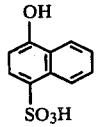 | copper | bordo |
| 22 | (B) | 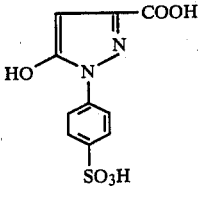 | copper | yellowish-brown |
| 23 | (B) | 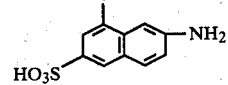 | Chromium | grey |
| 24 | 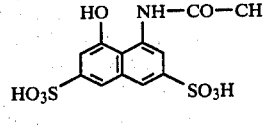 |  | copper | blue |

-continued

| Ex. | Compound of the Formula II | Coupling component | Metal | Color shade on cotton |
|---|---|---|---|---|
| 25 | " | (structure: naphthol with OH, HO3S, azo-linked to pyrazolone with COOH, HO, N-phenyl-SO3H) | copper | black |
| 26 | (A) | (structure: naphthol with OH, HO3S, NH-CO-CH2-CH2-SO3H) | copper | bluish red |
| 27 | (A) | (structure: HO, NH2, HO3S, SO3H naphthalene azo-linked to benzene with SO3H groups) | copper | marine blue |
| 28 | (A) | (structure: naphthol OH, HO3S azo-linked to HO, NH2, SO3H, SO3H naphthalene) | copper | marine blue |
| 29 | (A) | (structure: naphthol OH, HO3S azo-linked to HO, NH—COCH3, HO3S, SO3H naphthalene) | copper | marine blue |
| 30 | (A) | (structure: pyrazole with CH3, HO, N-(Cl, CH3, SO3H-phenyl)) | cobalt | reddish-yellow |
| 31 | (A) | (structure: naphthalene with OH, NH2, HO3S) | nickel | brown |

EXAMPLES GROUP B

EXAMPLE 1

(a) 3200 parts by weight of 4-amino-3'-($\beta$-hydroxyethylsulfonyl)-benzanilide in the form of a dry powder were introduced into a customary commercial dispersion kneader (for example of the firm Werner and Pfleiderer, Stuttgart-Feuerbach), the kneading arms of which operated at a speed of 29 and 21 revs/min respectively. Then, with the machine running, 1071 parts by weight of 65% strength oleum were introduced in a very thin jet over a period of 45 minutes. By means of temperature regulation by the heating and cooling jacket, the reaction mixture was left for a further 2 hours in the running kneader at a temperature of 80°–100° C., then cooled to below 40° C. and removed from the kneader.

4100 parts by weight of a light brownish-grey colored powder were obtained, which powder was 92% strength of 4-amino-3'-($\beta$-sulfatoethylsulfonyl)-benzanilide having a molecular weight of 400. The degree of esterification was 97–98%.

(b) 2.0 parts by weight of the kneaded material were stirred into a mixture of 16 parts by volume of water and four parts by weight of ice at 0° to 5° C. with the simultaneous portionwise addition of approximately 0.65 parts by weight of sodium bicarbonate. The pH value of the aqueous solution thus obtained was 5.0 to 5.5; the solution was clarified by filtration and evaporated to dryness in vacuo at 60° to 65° C., and ground. 2.1 parts by weight of a powder were obtained, which, together with 8% by weight of sodium sulfate, contained the pure compound of the formula lowing Table, likewise in a high yield, of a high degree of purity and with a high degree of esterification, the corresponding sulfuric acid semi esters of the formulae below (end products).

| Example | Starting compound | End product |
|---|---|---|
| 4 | 4-($SO_2$-$CH_2$-$CH_2$-OH)-phenyl—NH—CO—phenyl-$NH_2$ | 4-($SO_2$-$CH_2$-$CH_2$-$OSO_3H$)-phenyl—NH—CO—phenyl-$NH_2$ |
| 5 | 3-($SO_2$-$CH_2$-$CH_2$-OH)-phenyl—NH—CO—(3-aminophenyl) | 3-($SO_2$-$CH_2$-$CH_2$-$OSO_3H$)-phenyl—NH—CO—(3-aminophenyl) |
| 6 | 4-($SO_2$-$CH_2$-$CH_2$-OH)-phenyl—NH—CO—(3-aminophenyl) | 4-($SO_2$-$CH_2$-$CH_2$-$OSO_3H$)-phenyl—NH—CO—(3-aminophenyl) |

3-($SO$-$CH_2$-$CH_2$-$OSO_3H$)-phenyl—NH—CO—(4-aminophenyl)

in the form of its sodium salt.

EXAMPLE 2

3200 parts by weight of 4-amino-3'-(β-hydroxyethyl-sulfonyl)-benzanilide in the form of a dry powder were introduced into a customary commercial dispersion kneader. With the machine running, 2111 g of 100% strength sulfuric acid were introduced over a period of 40 minutes; the temperature remained below 100° C. The reaction mixture was kneaded for a further 2 hours at 80°–100° C. in the kneader, then cooled to below 40° C. and removed from the kneader. 5080 parts by weight of a pulverulent product were obtained, which product was 75% by weight of 4-amino-3'-(β-sulfatoethylsulfonyl)-benzanilide. The degree of esterification was 95%.

The kneaded material obtained can be worked up in a manner analogous to that in Example 1b.

EXAMPLE 3

23.1 g/min of 4-amino-3'-(β-hydroxyethylsulfonyl)-benzanilide in the form of a dry powder were introduced by way of a metering worm, and 6.2 ml/min of 65% strength oleum by means of a metering pump, into a customary commercial, continuously operating kneader (for example, the BUSS-Ko kneader, Type PR 46 of Buss AG., Basle, Switzerland), which operated at 26 revs/min. The kneader was maintained at a temperature of 100° to 110° C. by means of jacket heating and cooling. The kneaded material produced had a content of 82% by weight of 4-amino-3'-(β-sulfatoethylsulfonyl)-benzanilide having a molecular weight of 400. The degree of esterification was 97%.

The kneaded material obtained can be worked up in a manner analogous to that in Example 1b.

EXAMPLES 4–6

By proceeding in a manner analogous to that described in Examples 1, 2 or 3, in Examples 4–6 there are obtained from the starting compounds given in the fol-

EXAMPLE 7

87 parts by weight of the kneaded material produced in Example 1a were dissolved in 800 parts by volume of water, with the addition of a sodium carbonate solution, at a pH of 6.5 to 7; subsequently 44.0 parts by volume of a 5 N sodium nitrite solution were added and the solution thus produced was introduced, while stirring, into a mixture of 400 parts by weight of ice and 60 parts by volume of 31% strength hydrochloric acid. After stirring for one hour, the nitrite excess was destroyed with 2 parts by weight of amidosulfonic acid. 136.3 parts by weight of 53% strength 1-acetylamino-8-hydroxynaphthalene-3,6-disulfonic acid were added and the pH value of the reaction solution was increased to 5 within 30 minutes with 20 parts by weight of crystalline sodium acetate as well as, additionally, with sodium carbonate. Once the coupling was complete, the dyestuff solution obtained was clarified by the addition of 20 parts by weight of kieselguhr and evaporated at 60° C.

The residue was ground; 280 parts by weight of a dark red powder were obtained, which powder was 55% by weight of dyestuff of the formula

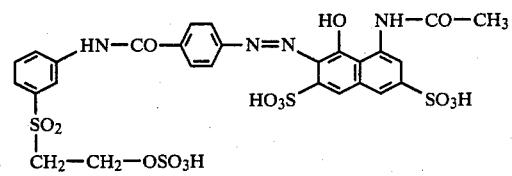

This dyestuff produced on cellulose fiber materials, such as, for example, on cotton, in the presence of agents having an alkaline action and using dyeing methods known and customary for reactive dyestuffs, brilliant, strong-colored, bluish-red dyeings and prints of a good fastness to light and of very good fastness properties to wetting.

EXAMPLE 8

If the 1-acetylamino-8-hydroxynaphthalene-3,6-disulfonic acid in Example 7 is replaced by the equimolar amount of 1-(4'-sulfophenyl)-3-carboxypyrazol-5-one, and the procedure is otherwise as described in Example 7, a yellow dyestuff is obtained which in the form of the free acid has the following formula:

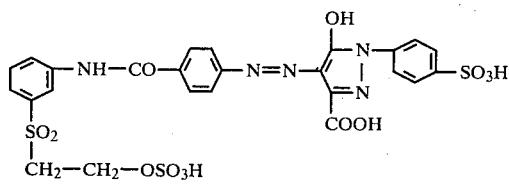

The product yielded on cotton, using the dyeing methods known and customary for reactive dyestuffs, strongly colored, yellow dyeings and prints of excellent fastness to light and to wetting.

EXAMPLES 7a AND 8a

The dyestuffs described in the above Examples 7 and 8 can be produced in an analogous or identical manner using the sulfuric acid semi ester synthesized according to Examples 2 and 3.

Examples 4a–6a

By replacing the sulfuric acid semi ester compound produced according to the invention, functioning as the diazo component in Examples 7 and 8 or 7a and 8a, by an equimolar amount of the sulfuric acid semi esters of Examples 4, 5 or 6 produced according to the invention, corresponding fiber-reactive azo dyestuffs are obtained which, using dyeing and printing methods known for reactive dyestuffs, likewise produce on cellulose fiber materials, such as cotton, strong-colored dyeings and prints of equally good properties of fastness to light and to wetting.

EXAMPLES GROUP C

EXAMPLE 1

(a) 3030 parts by weight of 1-[4'-(β-hydroxyethylsulfonyl)-phenyl]-3-methylpyrazol-5-one (94% strength) in the form of a dry powder were introduced into a customary commercial dispersion kneader (for example, of the firm Werner and Pfleiderer, Stuttgart-Feuerbach), of which one kneading arm operated at a speed of 29 revs/min and the other kneading arm at a speed of 21 revs/min. Then, with the machine running, 1071 parts by weight of 65% strength oleum (that is, 65 parts by weight of SO₃ and 35 parts by weight of H₂SO₄ per 100 parts by weight of oleum) were introduced over a period of 10 minutes. Subsequently the reaction mixture was worked in the kneader for a further two hours at 120° to 130° C., then the kneader was emptied. 4000 parts by weight of a light powder, which powder contained 91% of 1-[4'-(β-sulfatoethylsulfonyl)-phenyl]-3-methylpyrazol-5-one, were obtained, corresponding to a theoretical yield of 99%.

(b) 2.0 parts by weight of the kneaded material were stirred into a mixture of 8 parts by volume of water and 2 parts by weight of ice at 0° to 5° C. with the simultaneous portionwise addition of approximately 0.6 parts by weight of sodium bicarbonate. The pH value of the aqueous solution thus obtained was 5.0 to 5.5; the solution was clarified by filtration and evaporated to dryness in vacuo at 60° to 65° C. By grinding, 2.1 parts by weight of a white powder were obtained, which contained in addition to 8% by weight of sodium sulfate, the pure compound of the formula

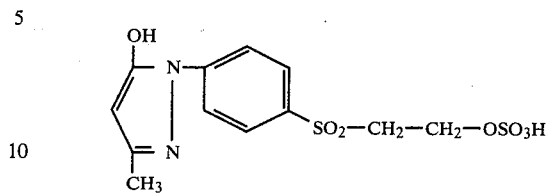

in the form of its sodium salt.

EXAMPLE 2

138.3 parts by weight of 2-aminonaphthalene-1,5-disulfonic acid (54.8% strength) were diazotized in a mixture of 300 parts by volume of water, 300 parts by weight of ice and 75 parts by volume of 31% strength hydrochloric acid at 0°–10° C. with 50 parts by volume of aqueous 5 N-sodium nitrite solution.

100 parts by weight of the kneaded material obtained according to Example 1a were dissolved in 500 parts by volume of water with the addition of 20 parts by weight of anhydrous sodium carbonate at a pH value of 5–6. This solution was added to the suspension of the diazonium salt. The pH value was adjusted to 3.5 to 4.0 with 40 parts by weight of anhydrous sodium carbonate. Once coupling was complete the temperature was gradually increased to 60°–70° C. and the solution was clarified with 10 g of kieselguhr. The filtrate was adjusted to a pH value of 4.8–5.3 with anhydrous sodium carbonate and subsequently evaporated to dryness at 50°–60° C. The residue was ground; 278 parts by weight of a yellow powder were obtained, which powder was 61% strength of the dyestuff of the formula

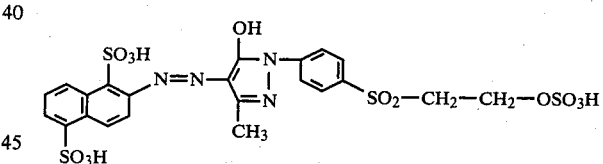

This dyestuff produces on cotton and other cellulose fiber materials in the presence of an agent having an alkaline action by dyeing and printing methods known and customary for reactive dyestuffs, strong-colored, clear, greenish-yellow dyeings and prints of very good fastness to light and wetting.

A dyestuff powder of the same dyestuff content and the same good quality is obtained by spray-drying the clarified dyestuff solution obtained in the preparation process instead of evaporating it.

EXAMPLE 3

By replacing the 138.3 parts by weight of 54.8% strength 2-aminonaphthalene-1,5-disulfonic acid used as diazo component in Example 2 by the equimolar amount of 2-aminonaphthalene-6,8-disulfonic acid and proceeding otherwise as described in Example 2, 260 parts by weight of a yellow dyestuff powder with a content of 65% by weight of the dyestuff of the formula

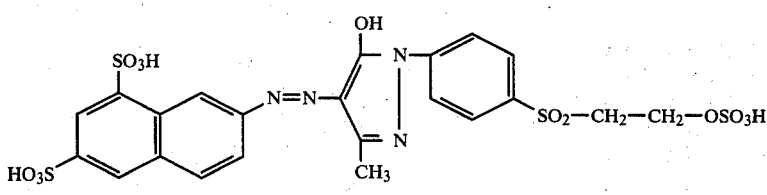

are obtained. This dyestuff produces on cotton, in the presence of an agent having an alkaline action in dyeing and printing processes known and customary for reactive dyestuffs, strong-colored, yellow dyeings and prints of very good fastness to light and to wetting.

EXAMPLE 4

3082 parts by weight of 1-[4'-($\beta$-hydroxyethylsulfonyl)-phenyl]-3-methylpyrazol-5-one (91.5% strength) in the form of a dry powder were introduced into a customary commercial dispersion kneader (for example, of the firm Werner and Pfleiderer, Stuttgart-Feuerbach). With the machine running, 2450 parts by weight of 100% strength sulfuric acid ("monohydrate") were introduced in the course of 20 minutes. By means of jacket heating the reaction temperature was increased to 125° C. and the mixture was left for 6 hours in the running kneader at this temperature. Then the kneader was emptied; 5400 parts by weight of 64% strength 1-[4'-($\beta$-sulfatoethylsulfonyl)-phenyl]-3-methylpyrazol-5-one were obtained.

The product thus produced can be worked up in a manner analogous to that described in Example 1b, or used for the production of reactive dyestuffs as described in Examples 2 and 3.

EXAMPLE 5

21.9 g/min of 1-[4'-($\beta$-hydroxyethylsulfonyl)-phenyl]-3-methylpyrazol-5-one (93% strength) in the form of a dry powder were introduced by way of a metering worm and 6.2 ml/min of 65% strength oleum by means of a metering pump, into a customary commercial, continuously operating kneader (for example, the BUSS-Ko kneader, type PR 46 of BUSS AG., Basle, Switzerland) which operated at 26 revs/min. The kneader was maintained at a temperature of 120° to 130° C. by means of steam heating the jacket. The kneaded material produced had a content of 77% by weight of 1-[4'-($\beta$-sulfatoethylsulfonyl)-phenyl]-3-methylpyrazol-5-one having a molecular weight of 362.

The kneaded material obtained can be worked up in a manner analogous to that described in Example 1b, or further processed, in a manner analogous to that in Example 2 or 3, into reactive dyestuffs.

EXAMPLE 6

37.8 parts by weight of 2-aminophenol-4-sulfonic acid were diazotized in a mixture of 150 parts by volume of water, 150 parts by weight of ice and 15 parts by weight of 100% strength sulfuric acid with the aqueous solution of 14 parts by weight of sodium nitrite. After stirring for one hour, a small nitrite excess was destroyed by adding a little amidosulfonic acid. 80 parts by weight of the kneaded material obtained according to Example 1a were introduced into this diazonium salt suspension; the pH value of the reaction mixture was adjusted to 6–7 with sodium carbonate and the coupling proceeded to completion at room temperature, while stirring, in the course of 15–20 hours. Subsequently 50 parts by weight of crystalline copper sulfate was added to this reaction mixture and the pH value were then adjusted to 4.5–5.5 with sodium carbonate. The conversion into the copper compound was complete after approximately one hour at room temperature; the dyestuff solution was then clarified by means of 10 parts by weight of kieselguhr and the filtrate evaporated to dryness at 50°–60° C. in vacuo, and the residue ground.

210 Parts by weight of a yellow-brown dyestuff powder were obtained, which powder was 61% by weight of the dyestuff of the formula

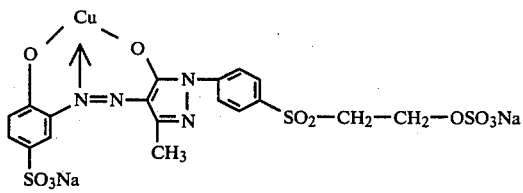

This dyestuff produces on cotton and other cellulose fiber materials, in the presence of an agent having an alkaline action in printing and dyeing processes known and customary for reactive dyestuffs, strong-colored, yellow-brown dyeings and prints of excellent fastness to light and wetting.

A dyestuff powder of the same content of dyestuff and the same good quality is obtained by spray-drying, instead of evaporating, the clarified dyestuff solution obtained in the preparation process.

EXAMPLE 7

By replacing the 50 parts by weight of crystalline copper sulfate in Example 6 by 50 parts by weight of chrome alum and boiling the reaction mixture under reflux for approximately 8 hours at a pH of 5–5.5, and evaporating the dyestuff solution at 60° C. and grinding the dry residue, a brown dyestuff powder of the 1:2 chromium complex dyestuff of the metal-free azo dyestuff of the formula

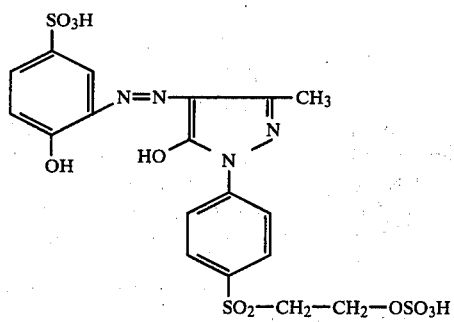

is obtained which produces on wool, or in the presence of an agent having an alkaline action on cotton, yellowish-red dyeings and prints with very good fastness properties.

EXAMPLE 8

By replacing the 50 parts by weight of crystalline copper sulfate in Example 6 by 28.1 parts by weight of crystalline cobalt sulfate and otherwise proceeding as described in Example 6, a dyestuff powder of the 1:2 cobalt complex dyestuff is obtained derived from the metal-free azo compound given in Example 7, in the form of its neutral sodium salt. The dyestuff produces on cotton in the presence of an agent having an alkaline action, strong-colored, reddish-yellow prints and dyeings with good fastness properties.

EXAMPLES 9 TO 29

By proceeding in a manner analogous to that in Example 1, 4 or 5, but starting from the compounds with X=OH given in the following Table, Examples 9 and 29, corresponding sulfuric acid semi-esters of the formulae (end products) given in the Table, in which X=$OSO_3H$, are obtained in high yield, of a high degree of purity and with a high degree of esterification. These sulfuric acid semi-ester compounds are excellently suitable, in a manner known per se, especially without intermediate isolation by the direct use of the kneaded material, as described in Examples 2 and 3 or 6 to 8, for the preparation of fiber reactive azo dyestuffs and their metal complex compounds.

Table of Examples 9 to 29
Compound of the formula

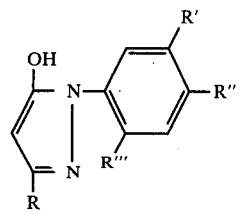

in which the radicals R' or R" are $-SO_2-CH_2-CH_2-X$, in which again the formula number X is OH in the starting material and X is $-OSO_3H$ in the end product, this end product having in each case a degree of esterification of between 96 and 99%.

| Ex. | R | R' | R" | R''' |
|---|---|---|---|---|
| 9 | —CH₃ | —SO₂—CH₂—CH₂—X | —H | —CH₃ |
| 10 | —COOH | —H | —SO₂—CH₂—CH₂—X | —H |
| 11 | —COOH | —SO₂—CH₂—CH₂—X | —H | —H |
| 12 | ⌬ | —H | —SO₂—CH₂—CH₂—X | —H |
| 13 | ⌬ | —SO₂—CH₂—CH₂—X | —H | —H |
| 14 | —CH₃ | —SO₂—CH₂—CH₂—X | —H | —H |
| 15 | —CH₃ | —SO₂—CH₂—CH₂—X | —H | —OCH₃ |
| 16 | —CH₃ | —CH₃ | —SO₂—CH₂—CH₂—X | —OCH₃ |
| 17 | —CH₃ | —OCH₃ | —SO₂—CH₂—CH₂—X | —OCH₃ |
| 18 | —CH₃ | —H | —SO₂—CH₂—CH₂—X | —Cl |
| 19 | —COOH | —SO₂—CH₂—CH₂—X | —H | —CH₃ |
| 20 | —COOH | —SO₂—CH₂—CH₂—X | —H | —OCH₃ |
| 21 | —COOH | —CH₃ | —SO₂—CH₂—CH₂—X | —OCH₃ |
| 22 | —COOH | —OCH₃ | —SO₂—CH₂—CH₂—X | —OCH₃ |
| 23 | ⌬ | —SO₂—CH₂—CH₂—X | —H | —CH₃ |
| 24 | ⌬ | —SO₂—CH₂—CH₂—X | —H | —OCH₃ |
| 25 | ⌬ | —CH₃ | —SO₂—CH₂—CH₂—X | —OCH₃ |
| 26 | ⌬ | —OCH₃ | —SO₂—CH₂—CH₂—X | —OCH₃ |
| 27 | ⌬ | —OCH₃ | —SO₂—CH₂—CH₂—X | —OCH₃ |

EXAMPLES 28 TO 42

Furthermore, it was possible, as can be seen from the following Table Examples, to produce in the manner according to the invention without intermediate isolation the following azo dyestuffs or metal complex dyestuffs from the compounds of the formula (II) obtained according to the process of the invention. Using analogously the methods described in Examples 2 or 3 or 6 to 8, but coupling a coupling component given in the following Examples, with the diazonium compound of the amino compound given in this Example, and converting then the azo product, if desired, into the corresponding metal complex compound by treating it with a copper, chromium or cobalt-donating metallising agent, and isolating the dyestuff thus obtained by evaporating or spray-drying of the dyestuff solution, dyestuffs (dyestuff powders) are obtained which yield on cotton strong-colored dyeings and prints in the color shades given in the respective Examples, which are fast to light and to wetting.

| Example | amino compound | Coupling component of Example | Color shade of the dyeing on cotton using the resulting dyestuff |
|---|---|---|---|
| 28 | 2-aminobenzenesulfonic acid (SO₃H ortho to NH₂) | 1 | greenish-yellow |
| 29 | 4-amino-benzenesulfonic acid (HO₃S para to NH₂) | 1 | " |
| 30 | 2-amino-5-chloro-4-sulfo-benzoic acid (SO₃H, NH₂, Cl, COOH substituted benzene) | 1 | " |
| 31 | [NiPc]–(SO₂—NH—C₆H₄—NH₂)₂,₂ –(SO₃H)₁,₈ | 1 | yellowish-green |
| 32 | 2-amino-4,5-dimethoxy-benzenesulfonic acid (OCH₃, CH₃O, NH₂, SO₃H) | 1 | reddish-yellow |
| 33 | anthranilic acid (COOH, NH₂ benzene) | 1 | greenish-yellow |
| 34 | 2-amino-3,5-dimethylbenzenesulfonic acid (SO₃H, NH₂, CH₃, CH₃) | 1 | " |
| 35 | 4′-sulfo-phenylazo-(2-amino-5-sulfo)benzene (HO₃S—C₆H₄—N=N—C₆H₃(SO₃H)—NH₂) | 10 | orange |
| 36 | 2-amino-1,5-naphthalenedisulfonic acid (SO₃H, NH₂, SO₃H on naphthalene) | 10 | yellow |
| 37 | " | 12 | yellow |
| 38 | 2-amino-1,5,7-naphthalenetrisulfonic acid (HO₃S, SO₃H, NH₂, SO₃H on naphthalene) | 1 | greenish yellow |
| 39 | 2-amino-4,6,8-naphthalenetrisulfonic acid (HO₃S, HO₃S, NH₂, SO₃H on naphthalene) | 22 | reddish-yellow |
| 40 | 2-amino-1-hydroxy-4-sulfo-benzene (OH, NH₂, HO₃S) | Example 10, then converted by copper sulfate into the Cu-complex dyestuff | yellow-brown |
| 41 | 2-amino-1-hydroxy-4-methoxy-benzene (OH, NH₂, OCH₃) | Example 12, then converted by Cr(III)-chloride into the 1:2 chromium complex dyestuff | red |

| Example | amino compound | Coupling component of Example | Color shade of the dyeing on cotton using the resulting dyestuff |
|---|---|---|---|
| 42 | 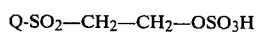 | Example 17, then converted by cobalt sulfate into the 1:2 cobalt complex dyestuff | reddish-yellow |

We claim:

1. In a process for the preparation of a compound of the formula

Q-SO₂—CH₂—CH₂—OSO₃H in which Q- represents a radical of the formula

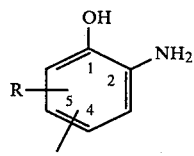

of the formula

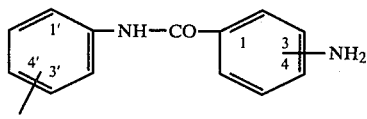

or of the formula

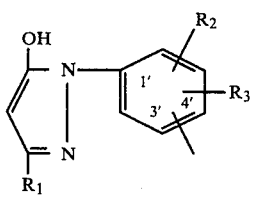

in which R is hydrogen, lower alkoxy, lower alkyl, nitro, chlorine, or bromine, R₁ is methyl, carboxyl or phenyl, R₂ is hydrogen, methyl, ethyl, methoxy, ethoxy or chlorine, and R₃ is hydrogen, methyl, ethyl, methoxy or ethoxy, the β-sulfatoethylsulfonyl group is in the 4- or 5-position of the benzene nucleus of the aminophenol or in the 3'- or 4'-position of the benzene nucleus and the amino group is bonded in the 3- or 4-position to the benzene nucleus of the benzoyl radical, by the esterification of a compound of the formula

Q-SO₂—CH₂—CH₂—OH, in which Q- and R, R₁, R₂ and R₃ therein have the meanings given above and the β-hydroxyethylsulfonyl group is in the 4- or 5-position of the benzene nucleus of the aminophenol or in the 3'- or 4'-position of the benzene nucleus, and the amino group is bonded in the 3- or 4-position to the benzene nucleus of the benzoyl radical, the improvement which comprises carrying out the esterification in a machine operating with a kneading action and with the action of 1 to 2.5 times the equimolar amount, calculated on SO₃, of sulfur trioxide or sulfuric acid containing sulfur trioxide.

2. A process according to claim 1, wherein a compound of the formula

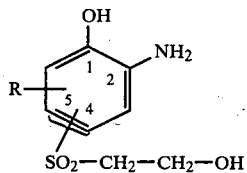

in which R has the meaning given in claim 1, and the β-hydroxyethylsulfonyl group stands in the 4- or 5-position of the benzene nucleus, is esterified to form the compound of the formula

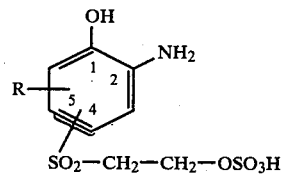

in which R has the meaning given in claim 1, and the β-sulfatoethylsulfonyl group is in the 4- or 5-position of the benzene nucleus.

3. A process according to claim 1, wherein a compound of the formula

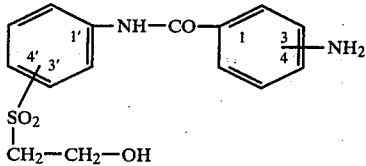

in which the amino group is in the 3- or 4-position of the benzoyl radical and the β-hydroxyethylsulfonyl group is in the 3'- or 4'-position of the anilide radical, is esterified to form the compound of the formula

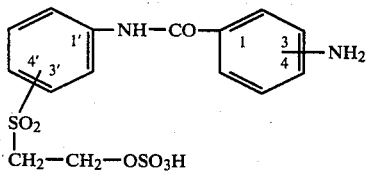

in which the amino group is in the 3- or 4-position of the benzoyl radical and the β-sulfatoethylsulfonyl group is in the 3'- or 4'-position of the anilide radical.

4. A process according to claim 1, wherein a compound of the formula

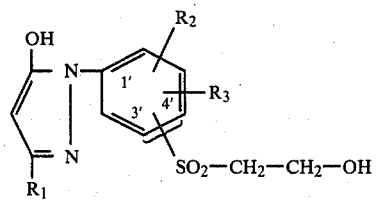

in which $R_1$, $R_2$, and $R_3$ have the meanings given in claim 1 and the β-hydroxyethylsulfonyl group is in the 3'- or 4'-position of the benzene nucleus is esterified to form the compound of the formula

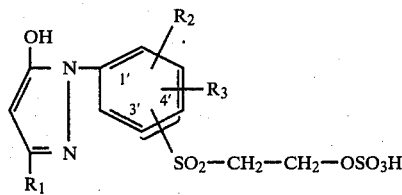

in which $R_1$, $R_2$ and $R_3$ have the meanings given in claim 1 and the β-sulfatoethylsulfonyl group is in the 3'- or 4'-position of the benzene nucleus.

5. A process according to claim 1, wherein 2-aminophenol-4-β-hydroxyethylsulfone is esterified to form 2-aminophenol-4-β-sulfatoethylsulfone.

6. A process according to claim 1, wherein 2-aminophenol-5-β-hydroxyethylsulfone is esterified to form 2-amino-5-β-sulfatoethylsulfonylphenol.

7. A process according to claim 1, wherein 2-aminophenol-4-methyl-5-β-hydroxyethylsulfone is esterified to form 2-aminophenol-4-methyl-5-β-sulfatoethylsulfone.

8. A process according to claim 1, wherein 2-aminophenol-4-methoxy-5-β-hydroxyethylsulfone is esterified to form 2-aminophenol-4-methoxy-5-β-sulfatoethylsulfone.

9. A process according to claim 1, wherein 4-amino-3'-(β-hydroxyethylsulfonyl)-benzanilide is esterified to form 4-amino-3'-(β-sulfatoethylsulfonyl)-benzanilide.

10. A process according to claim 1, wherein 1-[4'-(β-hydroxyethylsulfonyl)-phenyl]-3-methylpyrazol-5-one is esterified to form 1-[4'-(β-sulfatoethylsulfonyl)-phenyl]-3-methylpyrazol-5-one.

11. A process according to claim 1, wherein the esterification is carried out with 15–70% strength oleum.

12. A process according to claim 1, wherein the esterification is carried out with 1.1 to 1.5 times the molar amount, calculated on one mol of $SO_3$, of the esterification agent.

13. In a process for the preparation of a compound of the formula

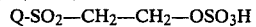

Q-SO$_2$—CH$_2$—CH$_2$—OSO$_3$H in which Q- represents a radical of the formula

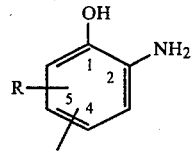

or of the formula

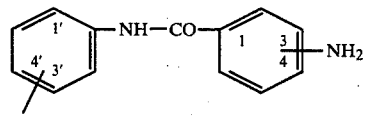

or of the formula

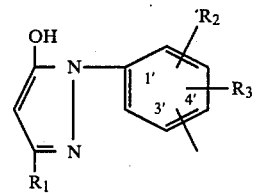

in which R is hydrogen, lower alkoxy, lower alkyl, nitro, chlorine, or bromine, $R_1$ is methyl, carboxyl or phenyl, $R_2$ is hydrogen, methyl, ethyl, methoxy, ethoxy or chlorine, and $R_3$ is hydrogen, methyl, ethyl, methoxy or ethoxy, the β-sulfatoethylsulfonyl group is in the 4- or 5-position of the benzene nucleus of the aminophenol or in the 3'- or 4'-position of the benzene nucleus and the amino group is bonded in the 3- or 4-position to the benzene nucleus of the benzoyl radical, by the esterification of a compound of the formula

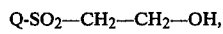

Q-SO$_2$—CH$_2$—CH$_2$—OH, in which Q- and R, $R_1$, $R_2$ and $R_3$ therein have the meanings given above and the β-hydroxyethylsulfonyl group is in the 4- or 5-position of the benzene nucleus of the aminophenol or in the 3'- or 4'-position of the benzene nucleus, and the amino group is bonded in the 3- or 4-position to the benzene nucleus of the benzoyl radical, the improvement which comprises carrying out the esterification in a machine operating with a kneading action and with the action of 1 to 2.5 times the equimolar amount, calculated on $SO_3$, of 92–100% strength sulfuric acid or sulfur trioxide or sulfuric acid containing sulfur trioxide.

* * * * *